United States Patent [19]
Lencer et al.

[11] Patent Number: 5,889,038
[45] Date of Patent: Mar. 30, 1999

[54] METHODS AND PRODUCTS FOR TREATING DIARRHEA AND SCOURS: USE OF CLOTRIMAZOLE AND RELATED AROMATIC COMPOUNDS

[75] Inventors: Wayne I. Lencer, Jamaica Plain; Carlo Brugnara, Newton Highlands; Seth Alper, Jamaica Plain, all of Mass.

[73] Assignee: Children's Hospital, Boston, Mass.

[21] Appl. No.: 621,169

[22] Filed: Mar. 20, 1996

[51] Int. Cl.$^6$ .......................... A61K 31/47; A61K 31/44; A61K 31/415; A61K 31/40; A61K 31/405; A61K 31/38; A61K 31/34

[52] U.S. Cl. .......................... 514/396; 514/312; 514/314; 514/332; 514/335; 514/339; 514/340; 514/341; 514/343; 514/397; 514/398; 514/399; 514/414; 514/415; 514/438; 514/444; 514/471; 514/473; 514/867

[58] Field of Search ...................................... 514/312, 314, 514/332, 335, 339, 340, 341, 343, 396, 397, 398, 399, 414, 415, 438, 444, 471, 473, 867

[56] References Cited

U.S. PATENT DOCUMENTS

| | | |
|---|---|---|
| 3,655,882 | 4/1972 | Wright et al. ............................ 424/147 |
| 3,965,112 | 6/1976 | White et al. .......................... 260/309.6 |
| 3,984,539 | 10/1976 | Khouw et al. ............................ 424/87 |

FOREIGN PATENT DOCUMENTS

| | | | |
|---|---|---|---|
| A-39340/89 | 8/1990 | Australia ...................... A61K 39/395 |
| A-52547/90 | 11/1990 | Australia ....................... A61K 37/02 |
| FR 2 715 068 A1 | 1/1994 | France . |
| DE 41 30 689 A1 | 3/1993 | Germany . |
| 62-163662 | 7/1987 | Japan . |
| WO91/15199 | 10/1991 | WIPO . |
| WO96/08242 | 3/1996 | WIPO . |
| WO97/04244 | 3/1997 | WIPO . |

OTHER PUBLICATIONS

Rufo, P., et al., "The Antifungal Antibiotic, Clotimazole, Inhibits Cl$^-$ Secretion by Polarized . . . ", *J. Clin. Invest.*, 1996, 98:9:2066–2075.

Rufo, P., et al., "Inhibition of K$^+$ Transport and C$^-$ Secretion in T84 Cells by Clotrimazole (CLT)", *J. General Physiology*, 1995, 106:38a, Abstract.

Mentzer, D., et al., "Parenterale Ernährung bei Gewichtsyerlust und chronischer Diarrhoe . . . " *Aids–Forschung AIFO—5th German Aids Congress*, 1994, 9:11:621 (#333) Abstract.

Peters, M., et al., "Die akute und chronische Diarrhö", *Med. Munatschr. Pharm.*, 1994, 17:12:358–366.

Brugnara C., et al., "Inhibition of CA2+–dependent K+ Transport and Cell Dehydration in Sickle . . . " *J. Clin. Invest.*, 1993, 92:1:520–526.

Simon, D., et al., "Treatment Options for AIDS–Related Espohageal and Diarrheal Disorders", *The American J. of Gastroenterology*, 1992, 87:3:274–281.

Smith, P., et al., "Gastrointestinal Infections in AIDS", *Annals of Internal Medicine*, 1992, 116:1:63–77.

Tzipori et al., "The Journal of Infectious Diseases" 1995; 171:1069–71 by The University of Chicago.

Verdon et al., "The Journal of Infectious Diseases" 1995; 171:1069–71 by The University of Chicago.

White et al., "The Journal of Infectious Diseases" 1995; 171:1069–71 by The University of Chicago.

A. Plattenberg, A. Stoehr, H.J. Stellbrink, H. Albrecht, W. Meigel "A preparation from bovine colostrum in the treatment of HIV–positive patients with chronic diarrhea" Clin. Investig.(1993) 71:42–45.

Glendon D. Sinks, et al., "Effects of lasalocid infection and growth in young dairy calves" JAVMA, vol. No. 12, 1947–1951 (1992).

J.A. Rump et al., "Treatment of diarrhoea in human immunodeficiency virus–infected patients with immunoglobulins from bovine colostrum" Clin. Investig. (1992) 75:588–594.

R. Fayer "Activity of sulfadimethoxine against cryptosporidiosis in dairy calves" J. Parasitol., 78(3), 1992, pp. 534–537.

A.J. Roussel Jr., et al., "Effect of ketoprofen on *Escherichia coli* heat–stable enterotoxin–induced diarrhea in calves" Am. J. Vet. Res., vol. 54, No. 12, Dec. 1993,(2088–2090).

Hadya S. Nagesha, et al., "A variant serotype G3 rotavirus in piglets", Journal of Medical Virology 38:79–85 (1992).

H.W. Moon, DVM, PhD "Mechanisms in the pathogenesis of diarrhea: a review", Journal of the American Veterinary Medical Association, v. 172, 443–448 (1978).

Travis C. McGuire, DVM, PhD, et al., "Failure of colostral immunoglobulin transfer in calves dying from infectious disease", Journal Amer. Veterinary Medical Assoc. 169(7), 712–718 (1976).

Denis Archambault, DVM, PhD, et al., "Immune response of pregnant heifers and cows to bovine rotavirus inoculation and passive protection to rotavirus infection in newborn calves fed colostral antibodies or colostral lymphocytes", Am. J. Vet. Res., vol. 49, No. 7, 1084–1091 (1988).

Dale L. Haggard, DVM, MS, "Bovine enteric colibacillosis", Vet. Clinc. Of N. Am.: Food Animal Practice vol. 1, No. 3, 495–508 (1985).

F. Bürki, et al., "Reduction of rotavirus–, coronavirus–and *E. coli*–associated calf–diarrheas in a large–size dairy herd by means of dam vaccination with a triple–vaccine", J. Vet. Med. B33,241–252 (1986).

(List continued on next page.)

*Primary Examiner*—Kimberly Jordan
*Attorney, Agent, or Firm*—Wolf, Greenfield & Saks, P.C.

[57] ABSTRACT

A method and product for treating and preventing diarrhea and scours is provided. The method involves treating a subject who has diarrhea, or scours, or is at risk of getting diarrhea or scours with an aromatic compound of the invention. The products of the invention are a veterinary preparation of the aromatic compound of the invention and an anti-scours agent, and a pharmaceutical preparation of the aromatic compound of the invention and an anti-diarrheal agent.

29 Claims, 2 Drawing Sheets

OTHER PUBLICATIONS

"Bovine rota–coronavirus–*Escherichia coli* antibody (Bovine Origin) first defense", Immucell Corp. Product Instruction Sheet (1990).

D. Waltner–Toews, S.W., et al., "A field of evaluate the efficacy of a combined rotavirus–coronavirus/*Escherichia coli* vaccine in dairy cattle", Can. J. Comp. Med 49:1–9 (1985).

B. Kaijser, et al., "Protection against acute, ascending pyelonephritis caused by *Escherichia coli* in rats, using isolated capsular antigen conjugated to bovine serum Albumin", Infection and Immunity, v. 39 pp. 142–146 (1983).

I. Hajer, BVSC, PhD, et al., "Antigens of bovine coronavirus strain LY–138 and their diagnostic properties", Am. J. Vet. Res., vol. 39, pp. 441–444 (1978).

Harald Brüssow, et al., "Cross–neutralizing antibodies induced by single serotype vaccination of cows with rotavirus", J. Gen. Virol. 69, 1647–1658 (1988).

R.C. Heel, R.N., et al., "Miconazole: a preliminary review of its therapeutic efficacy in systemic fungal infections", Drugs 19:7–30 (1980).

W. Ritter, et al., "Pharmacokinetic fundamentals of vaginal treatment with clotrimazole", Chemotherapy 28 (Suppl. 1):37–42 (1982).

Wolfgang Ritter, PhD., "Pharmacokinetic fundamentals of vaginal treatment with clotrimazole", Am. J. Obstet. Gynecol. Aug. 1, 1985 (945–947).

B. Duhm et al., "The pharmacokinetics of clotrimazole $^{14}C$", Postgraduate Medical Journal 50 (Jul. Suppl.) 13–16 (1974).

Lucia DeFranceschi et al., "Treatment with oral clotrimazole blocks $Ca^{2+}$–activated $K^+$ transport and reverses erythrocyte dehydration in transgenic SAD mice", J. Clin. Invest. vol. 93, 1670–1676 (1994).

Carlo Brugnara et al., "Inhibition of $Ca^{2+}$–dependent $K^+$ transport and cell dehydration in sickle erythrocytes by clotrimazole and other imidazole derivatives", J. Clin. Invest., vol. 92, 520–526 (1993).

Brugnara et al., "Ion channels and genetic diseases", Society of General Physiologists 48th Annual Symposium pp. 1–3 (1994).

Carlo Brugnara, et al., "Oral administration of clotrimazole and blockage of human erythrocyte $Ca^{++}$–Activated $K^+$ Channel: the imidazole ring is not required for inhibitory activity[1]", JPET 273:266–272, (1995).

Mana Vajanaphanich, et al., "Long–term uncoupling of chloride secretion from intracellular calcium levels by Ins(3, 4,5,6)P.", Nature vol. 371, 711–714 (1994).

Carlo Brugnara, et al., "Therapy with oral clotrimazole induces inhibition of the gardos channel and reduction of erythrocyte dehydration in patients with sickle cell disease", J. Clin. Invest. vol. 97, No. 5, 1227–1234 (1996).

E. Lohrmann et al., "A new class of inhibitors of cAMP–mediated $Cl^-$ secretion in rabbit colon, acting by the cAMP–Activated $K^+$ conductance", Pflügers Arch—Eur. J. Physiol. 429:517–530 (1995).

Ilko G. Iliev, et al., "Potassium channels in epithelial cells", Cellular and Molecular Biology Research, vol. 39, No. 6, pp. 601–611, (1993).

Kiertisin Dharmsathaphorn, et al., "Vasoactive intestinal polypeptide–induced chloride secretion by a colonic epithelial cell line", J. Clin. Invest., vol. 75, 462–471 (1985).

METHODS AND PRODUCTS FOR TREATING DIARRHEA AND SCOURS: USE OF CLOTRIMAZOLE AND RELATED AROMATIC COMPOUNDS

BACKGROUND OF THE INVENTION

Acute and chronic diarrheas represent a major medical problem in many areas of the world. Diarrhea is both a significant factor in malnutrition and the leading cause of death (5,000,000 deaths/year) in children less than five years old. Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel. The major medical consequences of diarrheal diseases include dehydration, acidosis, death and impaired growth.

Diarrhea in barn animals and pets such as cows, pigs and horses, sheep, goats, cats and dogs, also known as scours, is a major cause of death in these animals. Diarrhea can result from any major transition, such as weaning or physical movement. One form of diarrhea is characterized by diarrhea in response to a bacterial or viral infection and generally occurs within the first few hours of the animal's life.

Although the major consequences of diarrheal diseases are very similar, there are numerous causes of diarrhea. Secretory and exudative diarrhea are primarily caused by bacterial or viral infections. The most common diarrheal causing bacteria is enterotoxogenic E-coli (ETEC) having the K99 pilus antigen. Common viral causes of diarrhea include rotavirus and coronavirus. Other infectious agents include cryptosporidium, giardia lamblia, and salmonella, among others.

The treatment for diarrhea depends on the patient and the infection source. Diarrhea which is found in travelers to industrialized nations (travelers diarrhea) frequently is caused by bacterial pathogens which are acquired through ingestion of fecally contaminated food and/or water. Approximately 50–75% of these cases are attributed to ETEC. Although traveler's diarrhea is painful, it is generally not life-threatening and often the symptoms last only 3–5 days. The symptoms include urgent diarrhea, abdominal cramps, nausea and fever. The most effective course of treatment for traveler's diarrhea is the administration of antibiotics in conjunction with oral rehydration. It has been shown that prophylactic administration of antibiotics drastically reduces the number of travelers experiencing symptoms of diarrhea. However, routine administration of antibiotics is not suggested as it may cause resistant strains of a bacteria to develop. Other treatment methods include administration of bismuth subsalicylate, often taken in the form of Pepto-Bismal, diphenoxylate and loperamide.

Diarrhea in AIDS patients is a very serious condition which causes wasting and may be an important factor in the decline of these patients. AIDS patients often develop diarrhea due to enteric infections which their immune system is not capable of fighting off, but AIDS patients may also develop diarrhea by AIDS enteropathy. AIDS enteropathy is a disorder characterized by diarrhea without the involvement of secondary infections. It is caused by the human immunodeficiency virus (HIV) infection of the small bowel mucosal cells and colonic mucosal cells. The most common infective agent causing diarrhea due to enteric infection in AIDS patients in cryptosporidium. The methods for treating diarrhea in AIDS patients include administration of antibiotics and administration of immunoglobulins or an immunoglobulin enriched fraction of bovine colostrum. Colostrum, which is the first milk produced by mammals after birthing is enriched with antibodies.

Acute diarrhea or scours, is a main cause of death in many newborn barn animals such as calves and pigs. Scours is often caused by ETEC with a K99 pilus antigen. Infection with the ETEC causes hypersecretion of fluid and electrolytes. Hypersecretion in turn causes dehydration and pH imbalance which may result in death of the newborn calf or pig.

Newborn barn animals are also susceptible to viral infectious agents causing scours. Infections with rotavirus and coronavirus are common in newborn calves and pigs. Rotavirus infection often occurs within 12 hours of birth. Symptoms of rotaviral infection include excretion of watery feces, dehydration and weakness. Coronavirus which causes a more severe illness in the newborn animals, has a higher mortality rate than rotaviral infection. Often, however, a young animal may be infected with more than one virus or with a combination of viral and bacterial microorganisms at one time. This dramatically increases the severity of the disease.

Generally the best protection for a newborn barn animal from viral or bacterial infection is the consumption of colostrum. If the mother animal has been exposed to these infectious agents then the colostrum will contain antibodies, which are often sufficient to protect the newborn from contracting the diseases. Sometimes, however, this is not sufficient and the animals need further protection. A common method of treatment includes administration of a concentrated colostrum solution or an immunoglobulin fraction isolated from a colostrum solution. This oral treatment may be combined with rehydration salts. Although these methods have improved the morbidity and mortality rate of newborn animals having scours, there still exists a need for more effective treatments.

Certain imidazoles such as clotrimazole are agents which have been used both topically and systemically as antifungals. More recently, studies have identified other uses for such imidazoles. U.S. Pat. No. 5,273,992 revealed that these imidazoles regulate $Ca^{++}$ actuated $K^{+-}$ channels in erythrocytes, and are thus useful in treating sickle cell anemia, which involves the inhibition of potassium transport. These imidazoles have also been found to be effective in inhibiting endothelial and/or vascular smooth muscle cell proliferation. The results of this finding are described in U.S. Pat. No. 5,358,959 and U.S. Ser. No. 08/018,840, which discloses using clotrimazole for treating atherosclerotic and angiogenic conditions, respectively. Nonimidazole metabolites and analogs of the foregoing compounds also have been described as useful in treating the foregoing conditions (see U.S. Ser. Nos. 08/307,874 and 08/307,887).

SUMMARY OF THE INVENTION

The present invention provides methods and products for treating diarrhea and scours. It has been discovered that aromatic compounds are effective in treating patients with diarrhea. These compounds are potent inhibitors of secretagogue-stimulated transepithelial electrogenic chloride secretion in intestinal cells.

According to one aspect of the invention, a method for treating diarrhea of diverse etiology is provided. The method involves administering to a subject who is in need of such treatment, an aromatic compound of the invention in an amount effective to inhibit the diarrhea. Preferably the compound is administered orally in conjunction with oral rehydration fluids. The aromatic compounds useful in the invention have the following formula:

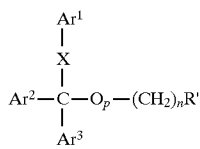

wherein n=0–3; wherein p=0 or 1; wherein X is selected from the group consisting of $(CH_2)_{m\ (m=0,1,2\ or\ 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar^1$ is selected from the group consisting of phenyl, substituted phenyl, and heteroaryl; wherein $Ar^2$ is selected from the group consisting of phenyl and substituted phenyl; wherein $Ar^3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=}1-5)$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, SH, $SCH_3$, $NH_2$, $NHCH_3$, and $N(CH_3)_2$; and wherein R" is selected from the group consisting of hydrogen and R.

In a preferred embodiment of the invention the aromatic compound is clotrimazole or a metabolite of clotrimazole.

A heteroaryl group includes but is not limited to furanyl, imidazole, pyridinyl, thiophenyl, indolyl, imidazolyl, and quinolyl.

Other aromatic compounds useful in the invention are miconazole and econazole.

In one embodiment of the invention the foregoing aromatic compounds may be administered in combination with other anti-diarrheal agents. In another embodiment the aromatic compounds may be administered in combination with other anti-scours agents.

According to one embodiment of the invention the subject in need of such treatment is a subject who has symptoms of diarrhea or scours. In another embodiment of the invention, the subject in need of such treatment is a subject at risk of developing diarrhea or scours.

According to another aspect of the invention, pharmaceutical preparations are provided. These pharmaceutical preparations include the aromatic compounds of the invention together with an anti-diarrheal agent. In one embodiment, the aromatic compounds useful according to the invention have the general formula provided above. In another embodiment, the aromatic compounds useful according to the invention are selected from the group consisting of miconazole and econazole. In yet another embodiment, the aromatic compounds useful according to the invention have the above-disclosed general formula, but wherein R' and $AR^1$ do not include imidazoles. Preferably the pharmaceutical composition of the invention may be administered orally.

According to another aspect of the invention, veterinary preparations are provided. These veterinary preparations include the aromatic compounds useful according to the invention together with an anti-scours preparation. In one embodiment, the aromatic compounds of the invention have the general formula provided above. In another embodiment, the aromatic compounds useful according to the invention are selected from the group consisting of miconazole and econazole. In yet another embodiment, the aromatic compounds useful according to the invention have the above-disclosed general formula, but wherein R' and $AR^1$ do not include imidazoles.

The invention also provides the aromatic compounds of the invention in the manufacture of a medicament for the treatment of diarrhea. In one embodiment, the aromatic compounds of the invention have the above-disclosed general formula, but do not include clotrimazole. In another embodiment, the aromatic compounds useful in the manufacture of a medicament for the treatment of diarrhea have the above-disclosed general formula, but wherein R' and $AR^1$ do not include imidazoles.

The invention also provides the aromatic compounds of the invention in the manufacture of a medicament for the treatment of scours. In one embodiment, the aromatic compounds of the invention have the above-disclosed general formula but do not include clotrimazole.

In another embodiment, the aromatic compounds useful in the manufacture of a medicament for the treatment of scours have the above-disclosed general formula, but wherein R' and $AR^1$ do not include imidazoles.

DETAILED DESCRIPTION OF THE INVENTION

Figure 1:
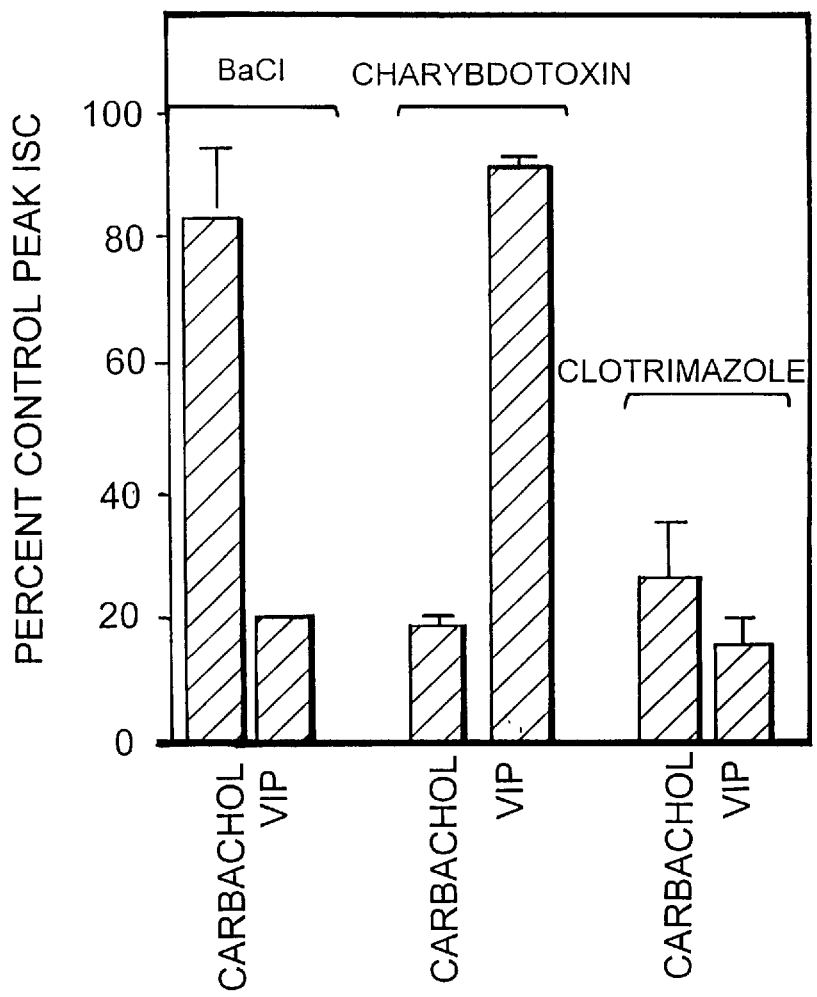
FIG. 1 is a bar graph depicting the effect of clotrimazole in the inhibition of cAMP and $Ca^{-+}$ dependent $Cl^-$ secretion in T84 cells.

The invention involves a method and product for reducing the symptoms of diarrhea or preventing diarrhea in a subject at risk for developing diarrhea. The compounds of the invention are aromatic compounds. The aromatic compounds useful according to the invention are provided in a pharmaceutical preparation and a veterinary preparation. The aromatic compounds of the invention are also useful in a method for treating diarrhea and scours as well as a method for preventing diarrhea and scours.

The aromatic compounds known to be useful in the invention have the following formula:

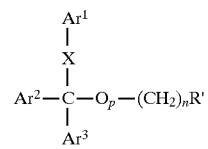

wherein n=0–3; wherein p=0 or 1; wherein X is selected from the group consisting of $(CH_2)_{m\ (m=0,1,2\ or\ 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar^1$ is selected from the group consisting of phenyl, substituted phenyl, and heteroaryl; wherein $Ar^2$ is selected from the group consisting of phenyl and substituted phenyl; wherein $Ar^3$ is selected from the group consisting of phenyl, substituted phenyl, biphenyl, bibenzyl, and naphthyl; wherein the phenyl substituent is selected from the group consisting of Cl, F, Br, I, R, OR", SR", NO$_2$, CN, CF$_3$, NR"R", and CO$_2$R; wherein R is selected from the group consisting of straight chain alkyl of C$_{z(z=1-5)}$, substituted straight chain alkyl of C$_{z(z=1-5)}$, branched alkyl of C$_{z(z=1-5)}$, and substituted branched alkyl of C$_{z(z=1-5)}$; wherein the alkyl substituent is selected from the group consisting of Cl, Br, F, I, OH, OCH$_3$, SH, SCH$_3$, NH$_2$, NHCH$_3$, and N(CH$_3$)$_2$; and wherein R" is selected from the group consisting of hydrogen and R.

A heteroaryl group includes but is not limited to furanyl, imidazole, pyridinyl, thiophenyl, indolyl, imidazolyl, and quinolyl.

In one embodiment the aromatic compound of the invention is clotrimazole, which has the following chemical structure:

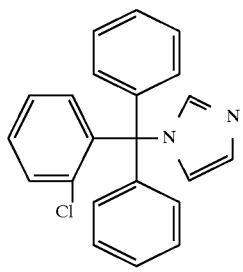

Other aromatic compounds believed useful according to the invention are clotrimazole metabolites, which have the following chemical structure:

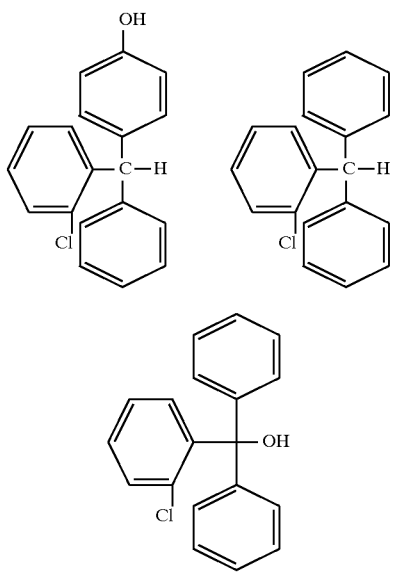

Other aromatic compounds believed useful according to the invention include miconazole and econazole which have the following structures:

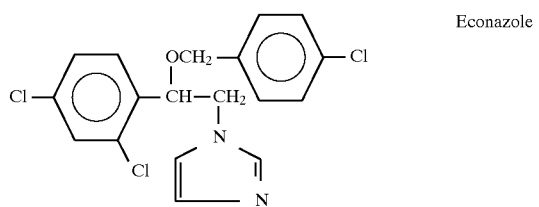

Econazole

-continued

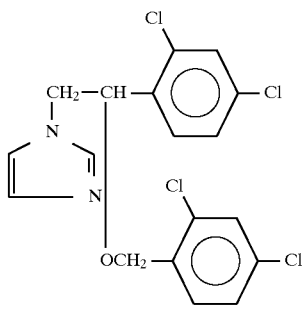

Miconazole

The aromatic compounds of the invention are commercially available compounds, are derived from commercially available compounds or are synthesized de novo using routine chemical synthetic procedures known to those of ordinary skill in the art.

Diarrhea, as used herein, indicates a medical syndrome which is characterized by the symptoms of diarrhea or scours. Diarrhea may be divided into three categories based on the underlying mechanism: exudative, decreased absorption, and secretory. Exudative diarrheas result from inflammatory processes leading to impaired colonic absorption, and outpouring of cells and colloid caused by such disorders as ulcerative colitis, shigellosis, and ambebiasis. Disorders of decreased absorption include osmotic, anatomic derangement, and motility disorders. Osmotic diarrhea can occur as a result of digestive abnormalities such as lactose intolerance. Anatomic derangement results in a decreased absorption surface caused by such procedures as subtotal colectomy and gastrocolic fistula. Motility disorders result from decreased contact time resulting from such diseases as hyperthyroidism and irritable bowel syndrome. Secretory diarrhea is characterized by the hypersecretion of fluid and electrolytes from the cells of the intestinal wall. In classical form, the hypersecretion is due to changes which are independent of the permeability, absorptive capacity and exogenously generated osmotic gradients within the intestine. However, all forms of diarrhea may manifest a secretory component.

The methods and products of the invention are particularly useful in treating diarrhea which is secretory. However, the methods and products of the invention may also be used in combination with other treatment methods which are known in the art to treat diarrhea caused by decreased absorption or inflammation. The compounds of the invention are involved in regulating Cl$^-$ secretion and can function alone or when used in combination with other treatment methods to decrease net fluid secretion even when this is due primarily to abnormalities in absorption or inflammation.

The methods and products of the invention are useful in preventing diarrhea and scours in subjects at risk of developing these disorders. Subjects at risk of developing diarrhea and scours are those subjects which have a high likelihood of exposure to the bacterial and viral microorganisms which cause these symptoms. For example, approximately ⅓ of travelers to developing countries will develop diarrhea; infection with rotavirus is one of the leading causes of death in infants in developing countries; patients with HIV have a greater than 50% chance of developing diarrhea, and many newborn calves and pigs develop scours. Patients with inflammatory bowel disease develop recurrent diarrhea.

The methods and products of the invention are also useful in treating subjects who already exhibit the symptoms of diarrhea and scours. Once a subject has been exposed to a microorganism causing the symptoms, the subject may be treated with the methods and products of the present invention in order to reduce the symptoms. The symptoms of diarrhea include bowel irregularity, fecal fluid rich in sodium or potassium, fluid feces, dehydration, fever, loss of body weight, headache, anorexia, vomiting, malaise and myalgia. The symptoms of scours include a loss of body weight or failure to grow, dehydration, malodorous feces, fluid feces, feces containing pieces of partially digested milk or semi-solid material, and feces of a yellow-white or gray color.

One product of the invention is a veterinary preparation of an aromatic compound of the invention, used alone or combined with an anti-scours agent. An anti-scours agent is a composition which is known to be useful in preventing or inhibiting the symptoms of scours. Known compositions include, for example, colostral extracts, such as those described in U.S. Pat. No. 4,377,569 and Canadian patent no. 1,175,352 and widely commercially available (e.g. Soluble Colostrum Powder, by VedCo, Inc., St. Joseph Mo.; Colostrum Bolus II, by RX Veterinary Products, Kansas City Mo., etc.); an immunological preparation of colostrum isolated from milk-producing mammals which may have been immunized against certain diarrheal causing microorganisms, such as those described in U.S. Pat. No. 4,834,974, Australian patent no. 39340/89, Australian patent no. 52547/90, and German patent no. 1,560,344; microorganism specific immunological preparations, including microorganism specific hybridoma-derived monoclonal antibodies such as those described in Sherman et al., *Infection and Immunity*, V. 42 (2), P. 653–658 (1983) and a bovine immunoglobulin fraction prepared from bovine plasma or clear bovine serum such as the fraction described in U.S. Pat. No. 3,984,539; oral rehydration fluids and/or replacement electrolyte compositions which are widely commercially available in the form of dry compositions or liquid solutions prepared for oral or intravenous administration (e.g. Electrolyte H, by Agri-Pet Inc., Aubrey Tex; Electrolyte Powder 8x, by Phoenix Pharmaceutical Inc, St. Joseph Mo.; Electrolyte Solution Rx, by Lextron Inc., Greeley Colo., ProLabs LTD, St. Joseph Mo., and VetTek Inc., Blue Springs Mo.; Calf Rehydrate, by Durvet Inc., Blue Springs Mo., etc.) and antibiotic compositions which are commercially available (e.g. BIOSOL® Liquid, by The UpJohn Company Animal Health Division, Kalamazoo Mich.; AMOXI-BOL®, by SmithKline-Beecham Animal Health, Exton Pa.; 5-WAY CALF SCOUR BOLUS™, by Agri Laboratories LTD, St. Joseph Mo.; 1-A-DAY CALF SCOUR BOLUS, by A.H.A.; GARACIN® PIG PUMP, by Schering-Plough Animal Health Corporation, Kenilworth N.J., etc.).

In one embodiment, the aromatic compounds useful in the veterinary preparation include miconazole, econazole, and the aromatic compounds of the general formula provided above.

In another embodiment, the aromatic compounds useful in the veterinary preparation include the aromatic compounds of the general formula provided above, but wherein R' and AR$^1$ do not include imidazoles.

In one embodiment, the veterinary preparation is a dry, preparation of the aromatic compound of the invention and an antiscours agent. The dry preparation may be administered directly or may be hydrated and/or diluted in a liquid solution prior to administration. In another embodiment, the veterinary preparation is a liquid solution of the compound of the invention and an anti-scours agent.

Another product of the invention is a pharmaceutical preparation of an aromatic compound of the invention and an anti-diarrheal agent. An anti-diarrheal agent includes, for example, an immunoglobulin preparation from bovine colostrum; lomotil; an intravenous or oral rehydration fluid; a dry rehydration composition salt; an electrolyte replacement composition (in dry or liquid form); an oral or intravenous sugar-electrolyte solution or dry composition; an antibiotic such as tetracycline, trimethoprim or sulfamethoxazole; a quinolone drug such as norfloxacin or ciprofloxacin, bismuth subsalicylate, diphenoxylate; and loperamide.

In one embodiment, the aromatic compounds useful in the pharmaceutical preparation include miconazole, econazole, and the aromatic compounds of the general formula provided above.

In another embodiment, the aromatic compounds useful in the pharmaceutical preparation include the aromatic compounds of the general formula provided above, but wherein R' and AR$^1$ do not include imidazoles.

In one embodiment the pharmaceutical preparation is a dry preparation of the aromatic compound of the invention and an anti-diarrheal agent. The dry preparation may be administered directly or may be hydrated and/or diluted in a liquid solution prior to administration. In another embodiment the pharmaceutical preparation is a liquid solution of the aromatic compound of the invention and an anti-diarrheal agent.

A subject as used herein, means humans, primates, horses, cows, sheep, pigs, goats, cats and dogs.

The time of administration of the aromatic compounds useful according to the invention varies depending upon the purpose of the administration. When the compounds of the invention are administered in order to prevent the development of diarrhea in subjects traveling to areas with high risk of exposure to infectious agent or subjects otherwise exposed to diarrhea causing agents, the compounds should be administered at about the time that the subject is exposed to the risk or the high risk area. When the compounds are administered to subjects in order to prevent the development of scours, the veterinary preparation should be administered within the first 12 hours after birth, and preferably within the first 4 hours after birth. When the compounds of the invention are used to treat subjects having symptoms of diarrhea or scours, the compounds may be administered at any point while the subject is experiencing symptoms, and preferably as soon as the symptoms develop.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be pharmaceutical compositions having a therapeutically effective amount of an aromatic compound of the general formula provided above in combination with an anti-diarrheal agent, optionally included in a pharmaceutically-acceptable carrier. The active compounds of the present invention also may be veterinary compositions having a therapeutically effective amount of an aromatic compound of the general formula provided above in combination with an anti-scours agent, optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the compound of the present invention, with the anti-diarrheal or anti-scours agents, and with each other, in a manner such that there is no interaction which would substantially impair the desired pharmaceutical efficacy.

A common administration vehicle (e.g., pill, tablet, bolus, powder or solution for dilution, pig pump, implant, injectable solution, etc.) would contain both the compounds useful in this invention and the anti-diarrheal or anti-scours agent. Thus, the present invention provides pharmaceutical or veterinary compositions, for medical or veterinary use, which comprise the active compounds of the invention together with one or more pharmaceutically acceptable carriers thereof and other therapeutic ingredients.

The formulations of the invention are administered in effective amounts. An effective amount is one sufficient to inhibit the $Cl^-$ secretion of intestinal epithelial cells, thereby effectively decreasing the secretory response, thereby resulting in a decrease in diarrhea or scours and/or the symptoms thereof. Effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used; that is, the highest safe dose according to sound medical judgment, particularly if acute diarrhea or scours are the dominant clinical manifestation.

Dosage may be adjusted appropriately to achieve desired drug plasma levels. Generally, daily oral doses of active compounds will be from about 0.01 milligrams/kg per day to 1000 milligrams/kg per day. It is expected that oral doses in the range of 50 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

A variety of administration routes are available. The particular mode selected will depend of course, upon the particular drug selected, the severity of the diarrhea or scours being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. They could, however, be preferred in emergency situations. Oral administration will be preferred for prophylactic treatment because of the convenience to the subject as well as the dosing schedule.

The compositions may conveniently be presented in unit dosage form and may be prepared by any of the methods well known in the art of pharmacy. All methods include the step of bringing the active compounds into association with a carrier which constitutes one or more accessory ingredients. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion. Active ingredients administered orally may be in any form suitable for oral administration, e.g., a pill, tablet, bolus, drinking solution, liquid or powder composition to be diluted or mixed with food, pig pump, etc.

Compositions suitable for parenteral administration conveniently comprise a sterile aqueous preparation of the active compound, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are mot limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Use of a long-term sustained release implant may be particularly suitable for treatment of diarrhea in immunodeficient patients, who need continuous administration of the compositions of the invention. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

EXAMPLES

Example 1

Clotrimazole inhibits water and electrolyte secretion in intestinal epithelial cells.

The biochemical basis of secretory diarrhea involves intestinal Cl⁻ secretion in intestinal crypt cells. Under normal conditions, Cl⁻ ions are maintained within intestinal crypt cells at levels above their electrochemical potential by primarily and secondarily active transport mechanisms such as the Na/K atpase pumps and Na/K/2Cl cotransporters. Cl⁻ is transported into the lumen from the intestinal crypt cells through apical Cl⁻ channels. Intracellular levels of $K^+$, cAMP, cGMP, and $Ca^{++}$ are all involved in regulating the secretory response.

T84 cells were used to determine whether clotrimazole regulates Cl⁻ secretion in intestinal crypt cells. T84 cells form confluent monolayers of columnar epithelia that exhibit high transepithelial resistances, polarized apical and basilateral membranes, and cAMP and $Ca^{++}$ regulated Cl⁻ secretory pathways analogous to those found in native intestine.

Methods

Growth of T84 cells: T84 cells obtained from ATCC were cultured and passaged in equal parts of dulbecco's modified eagle's medium (DMEM), 1 g/1D-glucose) and Hams F-12 nutrient mixture, supplemented with 5% newborn calve serum, 15% mM HEPES, 14 mM Na $HCO_3$, 40 mg/l penicillin, 8 mg/l ampicillin, 0.90 mg/l streptomycin. Cells were seeded at confluent density onto 0.33 $cm^2$ or 5 $cm^2$ Transwell inserts (Costar, Cambridge, Mass.) coded with dilute rat collagen solution as previously described (Lencer et al., *J. Clin. Invest.*, 92: 2941–2951 (1993); Lencer et al., *J. Cell Biol.* 117: 1197–1209 (1992). Transepithelial resistances attain stable levels (>1000 Ohms.$cm^2$) after 7 days. The development of high transepithelial resistances correlated with the formation of confluent monolayers with well-developed tight junctions as assessed by morphological analysis, and with the ability of monolayers to secrete Cl⁻ (Madara et al., *Gastro.* 92: 1133–1145 (1987).

Electrophysiology: Confluent monolayers were transferred to Hanks buffered salt solution containing (in g/liter) 0.185 $CaCl_2$, 0.098$MgSO_4$, 0.4 KCl, 0.06 $KH_2PO_4$, 8NaCl, 0.048 $Na_2HPO_4$, 1 g glucose, and 10 nM HEPES, pH 7.4). Serosal and mucosal reservoirs were interfaced with Calomel and Ag-Ag Cl electrodes via 5% agar ridges made with Ringer's buffer. Transepithelial resistance was measured using a dual voltage clamp device to apply 25 or 50 μA current pulses. Short circuit current (ISC) was calculated using Ohms law (Lencer et al., *J. Clin. Invest.* 92: 2941–2951 (1993); Lencer et al. *J. Cell Biol.* 117: 1197–1209 (1992).

Results:

Clotrimazole inhibits Cl⁻ secretion in T84 cells: Previous studies have shown that Cl⁻ secretion in T84 cells is controlled by cAMP and $Ca^{++}$ regulated $K^+$ efflux pathways which are biophysically and pharmacologically distinct from one another. Vasoactive intestinal peptide (VIP) is a cAMP mediated agonist of the $K^+$ channel. Carbachol is a $Ca^{++}$-dependent agonist of the $Ca^{++}$ regulated $K^+$ channels. Inhibitors of Cl⁻ secretion in T84 cells may be identified and the type of channel involved determined by measuring transepithelial resistances in T84 cells which have been treated with VIP or carbachol to stimulate Cl⁻ secretion.

T84 cells were grown as described above and Cl⁻ secretion was stimulated by the addition to the media of either carbachol or VIP. The cells were then treated with BaCl (3 mM), Charybdotoxin, or clotrimazole. The short circuit current (ISC) was determined for the various inhibitor treatments as a percentage of the control in the absence of inhibitor (FIG. 1). BaCl strongly inhibited the secretory response to the cAMP mediated agonist VIP, but had no apparent affect on the secretory response elicited by the $Ca^{++}$-dependent agonist carbachol. In contrast, the scorpion venom Charybdotoxin strongly inhibited the secretory response elicited by carbachol, but had minimal affects on Cl⁻ secretion elicited by VIP. However, clotrimazole inhibited the Cl⁻ secretory responses to both agonists (IC50's of 3 and 8 μM respectively). The inhibition was fully reversible, >95% (data not shown).

Figure 2:
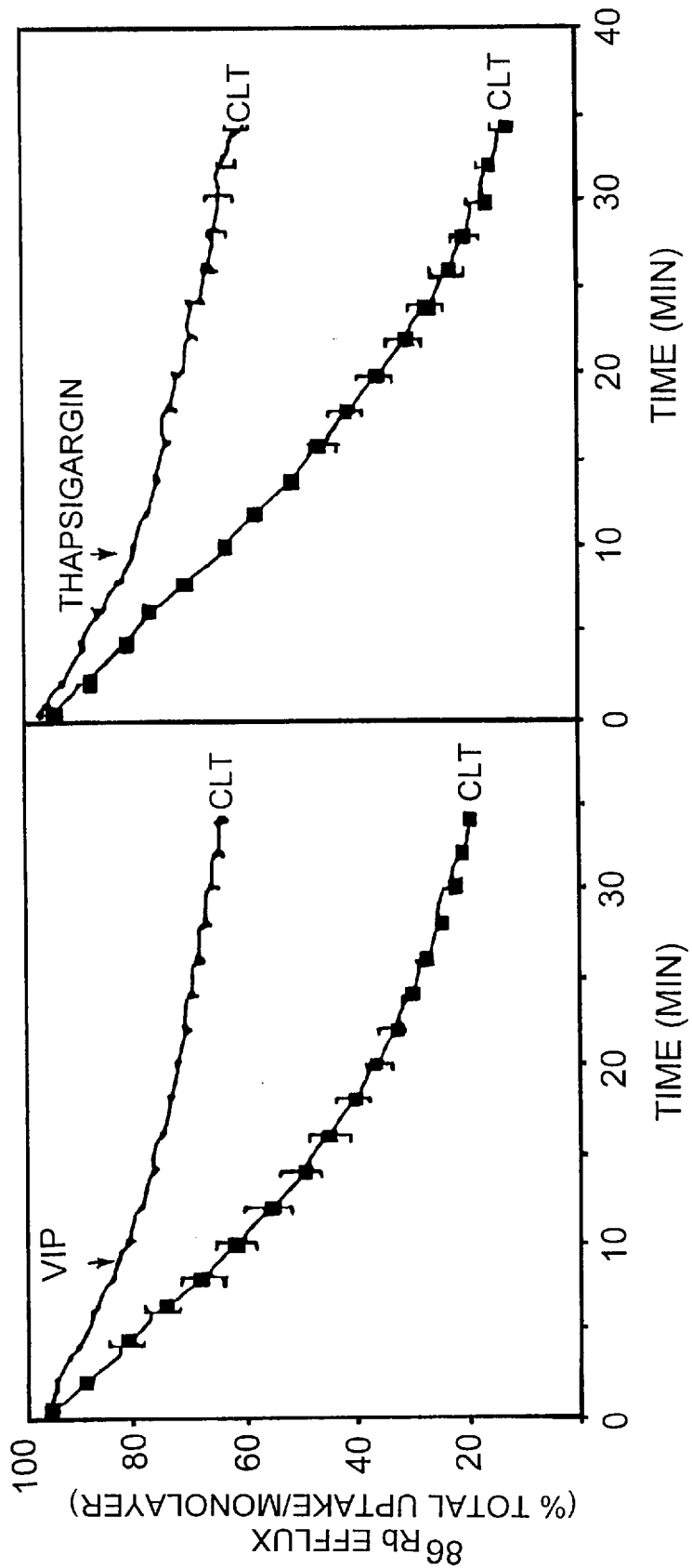
FIG. 2 is a graph showing the effect of clotrimazole on the inhibition of base line and $Ca^{++}$-stimulated $^{86}$Rb efflux from T84 monolayers.

The effect of clotrimazole on $K^+$ conductances was also examined by isotopic flux studies using $^{86}$RB (FIG. 2). T84 cells were grown in the presence of a cAMP agonist, VIP, or a $Ca^{++}$ mediated agonist (Thapsigargin). Clotrimazole was added and $^{86}$RB efflux was measured. FIG. 2 shows that clotrimazole significantly inhibits baseline and $Ca^{++}$ stimulated $^{86}$RB efflux in the presence of both cAMP and $Ca^{++}$ mediated agonists compared to those cells which were not treated with clotrimazole.

Taken together, these studies indicate that clotrimazole inhibits Cl⁻ secretion in T84 cells by both cAMP and $Ca^{++}$ mediated $K^+$ channels.

Example 2

Effect of clotrimazole on Cl⁻ secretion in in vivo systems.

20 adult New Zealand white rabbits are fasted for 12 hours prior to the time of experimentation. The animals are divided into equal (N=10 animals/group) control and clotrimazole (Gavage fed, 80 mg/kg/day) cohorts for a 2 day period after which the rabbits are anesthetized with ketamine (40–45 mg/kg) plus xylazine (5 mg/kg) plus atropine (0.2 mg/kg) I.M. The dosage of oral clotrimazole is within the range used in previous clinical trials in humans (Weuta, 14. Post Grad Med. J. (Supplement): 45–48 (1974). Segments of ileum are identified, surgically ligated and injected with either normal saline or saline containing cholera toxin (20 nM, a lumenally active secretagogue), and returned to the abdominal cavity. Animals then remain anesthetized in a 37° C. incubator for 4 hours, after which time secretion into the intestinal loops is measured gravimetrically and by direct fluid collection. Correction is made for secretion associated with surgical manipulation by subtracting the secretion measured from saline injected loops from that measured in loops treated with cholera toxin. Differences between control and clotrimazole treated loops are compared and tested for statistical significance using ANOVA.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for treating diarrhea or scours, the method comprising the step of:

administering to a subject in need of such treatment, an aromatic compound in an amount effective to inhibit the diarrhea, the aromatic compound having the general formula:

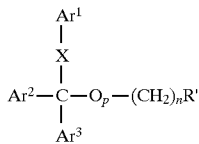

wherein n=0–3; wherein p=0 or 1; wherein X is selected from the group consisting of $(CH_2)_{m\ (m=0,1,2,\ or\ 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar^1$ is selected from the group consisting of phenyl, substituted phenyl, and heteroaryl; wherein $Ar^2$ is selected from the group consisting of phenyl and substituted phenyl; wherein $Ar^3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, SH, $SCH_3$, $NH_2$, $NHCH_3$, and $N(CH_3)_2$; and wherein R" is selected from the group consisting of hydrogen and R.

2. The method for treating diarrhea as in claim 1, wherein the aromatic compound is clotrimazole.

3. The method for treating diarrhea as in claim 1, wherein the aromatic compound is selected from the group consisting of:

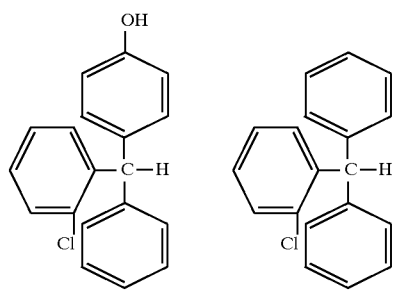

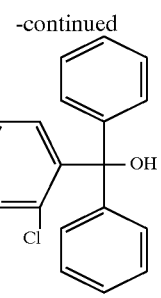

4. The method for treating diarrhea as in claim 1, wherein the aromatic compound is administered orally.

5. The method for treating diarrhea as in claim 1, wherein the subject is a human.

6. The method for treating diarrhea as in claim 5, further comprising administering an anti-diarrheal agent to the subject.

7. The method for treating diarrhea as in claim 6, wherein the anti-diarrheal agent is an oral rehydration fluid.

8. The method for treating diarrhea as in claim 1, wherein the subject is selected from the group consisting of a horse, a cow, a pig, and a goat.

9. The method for treating diarrhea as in claim 8, further comprising administering an anti-scours agent to the subject.

10. The method for treating diarrhea as in claim 1, wherein the aromatic compound is 2-chlorophenyl-bis-phenyl-methanol and has the following formula:

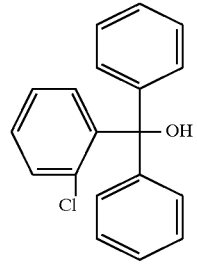

11. A veterinary preparation comprising:

an aromatic compound in an amount effective to inhibit scours in a subject, the aromatic compound having the general formula:

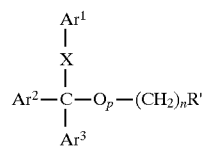

wherein n=0–3; wherein p=0 or 1; wherein X is selected from the group consisting of $(CH_2)_{m\ (m=0,1,2,\ or\ 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar^1$ is selected from the group consisting of phenyl, substituted phenyl, and heteroaryl; wherein $Ar^2$ is selected from the group consisting of phenyl and substituted phenyl; wherein $Ar^3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, $SH$, $SCH_3$, $NH_2$, $NHCH_3$, and $N(CH_3)_2$; and wherein R" is selected from the group consisting of hydrogen and R; and, an anti-scours agent.

12. A veterinary preparation as in claim 11, wherein the aromatic compound is clotrimazole.

13. The veterinary preparation as in claim 11, wherein the anti-scours agent is a colostral extract.

14. The veterinary preparation as in claim 11, wherein the anti-scours agent is an immunological preparation of colostrum.

15. The veterinary preparation as in claim 11, wherein the anti-scours agent is a microorganism specific immunological preparation.

16. The veterinary preparation as in claim 11, wherein the anti-scours agent is an oral rehydration fluid.

17. The veterinary preparation as in claim 11, wherein the anti-scours agent is a replacement electrolyte composition.

18. The veterinary preparation as in claim 11, wherein the anti-scours agent is an antibiotic composition.

19. The veterinary preparation as in claim 11, wherein the veterinary preparation is a dry preparation.

20. The veterinary preparation as in claim 11, wherein the aromatic compound is 2-chlorophenyl-bis-phenyl-methanol and has the following formula:

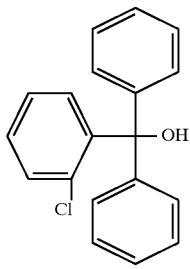

21. A pharmaceutical preparation, comprising:

an aromatic compound in an amount effective to inhibit diarrhea, the aromatic compound having the general formula:

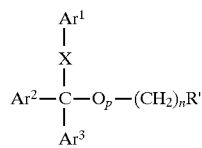

wherein n=0–3; wherein p=0 or 1; wherein X is selected from the group consisting of $(CH_2)_{m\ (m=1,2\ or\ 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar^1$ is selected from the group consisting of phenyl, substituted phenyl, and heteroaryl; wherein $Ar^2$ is selected from the group consisting of phenyl and substituted phenyl; wherein $Ar^3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, $SH$, $SCH_3$, $NH_2$, $NHCH_3$, and $N(CH_3)_2$; and wherein R" is selected from the group consisting of hydrogen and R; and, an anti-diarrheal agent.

22. The pharmaceutical preparation as in claim 21, wherein the aromatic compound is 2-chlorophenyl-bis-phenyl-methanol and has the following formula:

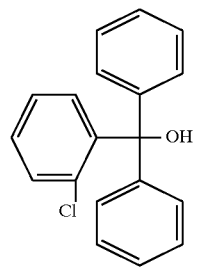

23. The pharmaceutical preparation as in claim 21, wherein the aromatic compound is clotrimazole.

24. She pharmaceutical preparation as in claim 21, wherein the anti-diarrheal agent is an oral rehydration fluid.

25. The pharmaceutical preparation as in claim 21, wherein the anti-diarrheal agent is an antibiotic.

26. The pharmaceutical preparation as in claim 21, wherein the anti-diarrheal agent is an electrolyte composition.

27. The pharmaceutical preparation as in claim 21, wherein the anti-diarrheal agent is an immunoglobulin preparation from bovine colostrum.

28. The pharmaceutical preparation as in claim 21, wherein the anti-diarrheal agent is an oral sugar-electrolyte solution.

29. A method for treating diarrhea or scours, the method comprising the step of:

administering to a subject in need of such treatment, an aromatic compound in an amount effective to inhibit diarrhea, the aromatic compound selected from the group consisting of miconazole and econazole.

* * * * *

UNITED STATES PATENT AND TRADEMARK OFFICE
CERTIFICATE OF CORRECTION

PATENT NO. : 5,889,038
DATED : March 30, 1999
INVENTOR(S) : Lencer et al.

It is certified that error appears in the above-identified patent and that said Letters Patent is hereby corrected as shown below:

Col. 1, line 5 the following should be inserted:

*This invention was made with government support under Grant No.(s) HL-15157 and T32DK07477 by the NIH. The government has certain rights in the invention.*

Signed and Sealed this

Twenty-first Day of March, 2000

Attest:

Q. TODD DICKINSON

Attesting Officer

Commissioner of Patents and Trademarks